(12) United States Patent
Marchal et al.

(10) Patent No.: US 6,960,288 B2
(45) Date of Patent: Nov. 1, 2005

(54) METHOD AND DEVICE FOR DETECTING MICROBIOLOGICALLY INDUCED CORROSION

(75) Inventors: Rémy Marchal, Chatou (FR); Nicolas Monfort-Moros, Paris (FR); Dominique Festy, Saint-Renan (FR); Bernard Tribollet, Malakoff (FR); Isabelle Frateur, Paris (FR)

(73) Assignees: Institut Francais du Petrole, Rueil Malmaison Cedex (FR); CNRS, Paris Cedex (FR); IFREMER, Issy-les-Moulineaux Cedex (FR)

( * ) Notice: Subject to any disclaimer, the term of this patent is extended or adjusted under 35 U.S.C. 154(b) by 178 days.

(21) Appl. No.: 10/258,861

(22) PCT Filed: Apr. 26, 2001

(86) PCT No.: PCT/FR01/01299

§ 371 (c)(1),
(2), (4) Date: Oct. 29, 2002

(87) PCT Pub. No.: WO01/86256

PCT Pub. Date: Nov. 15, 2001

(65) Prior Publication Data

US 2003/0085136 A1 May 8, 2003

(30) Foreign Application Priority Data

May 11, 2000 (FR) .......................................... 00 06114

(51) Int. Cl.$^7$ ............................................. G01N 27/416
(52) U.S. Cl. ................................... 205/775.5; 204/404
(58) Field of Search ....................... 205/775.5; 204/404

(56) References Cited

U.S. PATENT DOCUMENTS 4,863,572 A * 9/1989 Jasinski .................... 205/775.5
5,259,944 A * 11/1993 Feliu et al. ................. 204/404

* cited by examiner

*Primary Examiner*—Alex Noguerola
(74) *Attorney, Agent, or Firm*—Antonelli, Terry, Stout & Kraus, LLP

(57) ABSTRACT

The invention concerns a sensor and a method for detecting microbiologically induced corrosion in a metal structure, which consists in performing the following steps: providing a sensor comprising at least a first circular electrode (4) and a ring-shaped electrode (2) concentric with the first electrode, proximate to the structure (30) in contact with a corrosive medium; imparting for a time interval t a conditioning current between the two electrodes so as to initiate corrosion, the current being such that the central electrode is cathode and the ring-shaped electrode is anode; after the time interval t, coupling the two electrodes and measuring the current between the two electrodes; calculating the speed of corrosion from the measurement.

11 Claims, 4 Drawing Sheets

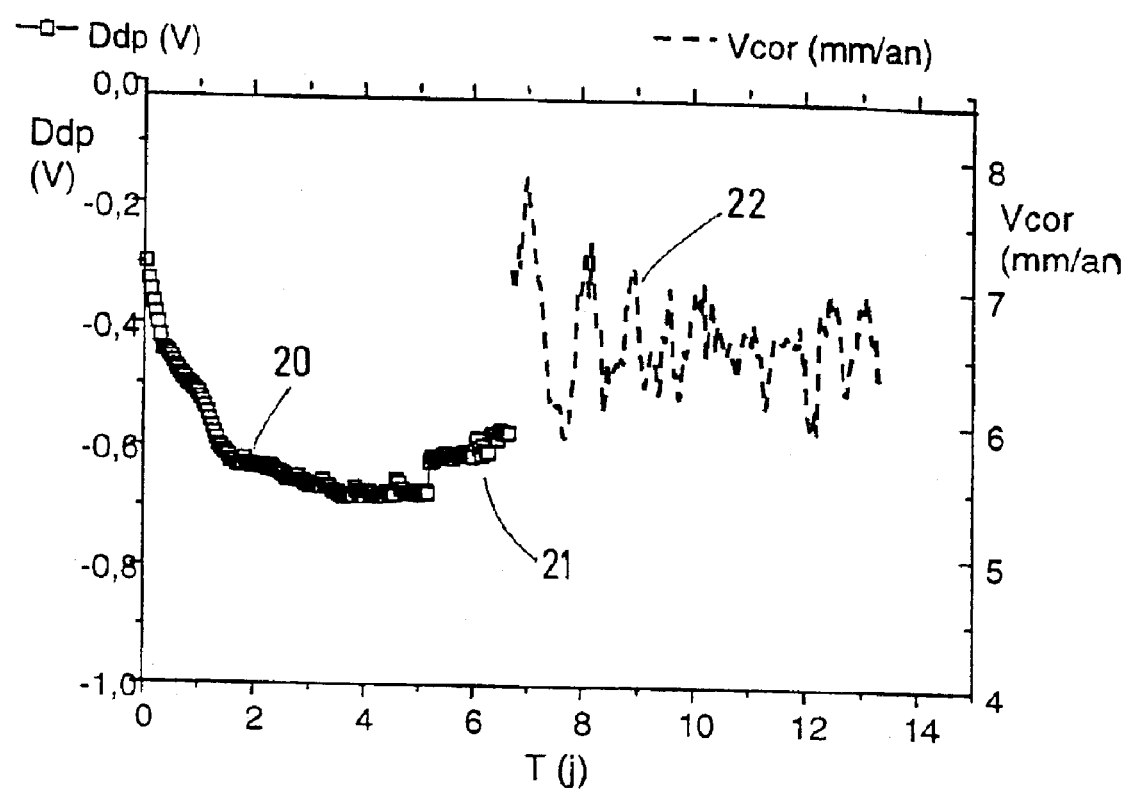

METHOD AND DEVICE FOR DETECTING MICROBIOLOGICALLY INDUCED CORROSION

BACKGROUND OF THE INVENTION

1. Field of the Invention

The present invention relates to a method of detecting microbiologically induced corrosion (M.I.C.) in industrial facilities, for example in the sphere of offshore structures: platforms, subsea pipes, wells, etc. Other spheres can also be concerned, such as the nuclear industry, harbour structures, geothermal facilities, the food-processing industry, among others.

2. Description of the Prior Art

The behavior of metal surfaces under working conditions can be followed by means of a programmer controlling the detector. According to the reaction of the detector towards the surrounding medium, a corrosive attack can be anticipated or detected, and facilities degradation can be anticipated.

In order to carry out a microbiologically induced corrosion experiment, it is necessary to have bacteria in a culture medium. The bacteria presently used belong to the *Desulfovibrio gabonensis* species (DSM 10636). The following document describes this bacterium: *Desulfiovibrio gabonensis* sp. Nov., "A New Moderately Halophilic Sulfate-Reducing Bacterium Isolated From An Oil Pipeline", by Tardy-Jacquenod C., Magot M., Laigret F., Kaghad M., Patel B.K.C., Guezennec J., Matheron R., Caumette P. (1996) Int. J. Syst. Bacteriol. 46:710–715.

The strain has a maximum growth for a pH value ranging between 6.9 and 7.3, a temperature of 30° C. and a NaCl salinity of 5 to 6%. It is strictly anaerobic, reduces sulfate to sulfide (hence the abbreviation S.R.B., Sulfate-Reducing Bacterium), and the substrates that are oxidized by the anaerobic respiration of the sulfur compounds are, among others, lactate and ethanol.

The latter point explains the corrosive character of such bacteria. In fact, it is not the bacteria themselves that attack the steel, but rather their metabolic products that deteriorate the metal structures.

The process is then sustained by the development of the bacteria which gather together and form a biofilm, and the corrosion rates can reach such values that one centimeter of steel can be pierced in less than a year.

SUMMARY OF THE INVENTION

The present invention thus relates to a method for detecting the microbiologically induced corrosion of a metal structure, wherein the following steps are carried out:

a detector comprising at least a first circular electrode and an annular electrode concentric to the first electrode is installed in a vicinity of the structure in contact with a corrosive medium, a conditioning current is applied for a time t between the two electrodes so as to initiate a corrosion, the current being such that the central electrode is cathode and the annular electrode is anode, after time t, the two electrodes are coupled and the current and/or the potential difference is measured between the two electrodes, a corrosion rate is calculated from the measurement.

The detector can comprise an auxiliary annular electrode interposed between the other two electrodes, the auxiliary electrode can be connected to the first central electrode during the conditioning stage, then it can be insulated from the other electrodes during the coupling stage.

The potential difference of the first electrode and/or of the second electrode in relation to the auxiliary electrode can be measured during the coupling stage.

A waiting stage wherein all the electrodes are insulated when the corrosion rate is below a determined threshold value can be established.

The invention also relates to a detector which detects microbiologically induced corrosion of a metal structure. The detector comprises a first circular electrode, a second annular electrode concentric to the first, means for applying a current between the two electrodes, means for measuring the current and/or the potential difference between the two electrodes.

Electronic control means successively carries out a conditioning stage wherein a current is applied between the two electrodes, the first electrode being cathode, the second electrode being an anode, then a measuring stage where the two electrodes are short-circuited.

An auxiliary annular electrode can be arranged between the first and the second electrode.

Connection means provide connection of the auxiliary electrode to the first electrode during the conditioning stage, and to insulate the auxiliary electrode from the other electrodes during the coupling stage.

All the electronic means can be self-contained and apply the conditioning stages and communicate measurements.

The material of the electrodes must be selected according to the material of the metal structure.

BRIEF DESCRIPTION OF THE DRAWINGS

Other features and advantages of the present invention will be clear from reading the description hereafter of tests given by way of non-limitative example, with reference to the accompanying drawings wherein:

FIG. 6 shows a graph of the measurements recorded during conditioning and coupling, FIG. 7 diagrammatically shows an example of application of the present invention.

It is well known, by experience, that biofilms develop more on cathodically polarized metal structures.

The main objective of electrochemistry is to localize and to initiate the microbiologically induced corrosion at the surface of a metallic electrode. Some electrochemistry notions are hereafter described.

Figure 1:
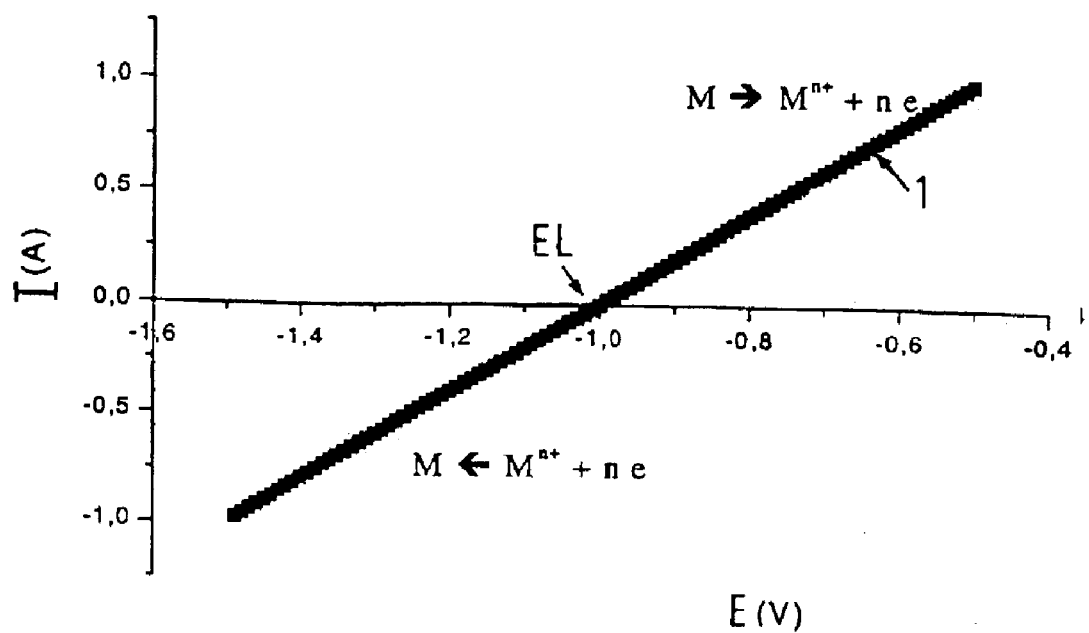
FIG. 1 shows an example of a polarization curve.

When a metallic electrode is dipped into a conducting medium, a polarization curve I/E (current=f(potential)), (reference 1, FIG. 1), can be drawn.

The part above the voltage axis corresponds to an anodic behavior of the electrode ($M \rightarrow M^{n+} + n\ e^-$) and the metal dissolves in the medium. The part below the voltage axis corresponds to a cathodic behavior of the electrode, where the cathodic reactions consume the $n\ e^-$ produced by the anodic reaction. The zero current potential (i.e. the potential when no current gets through the electrode) is called free potential or corrosion potential (E1).

Corrosion corresponds to a mostly anodic behavior and, in the configuration according to the present invention, two metallic electrodes are used.

Figure 2C:
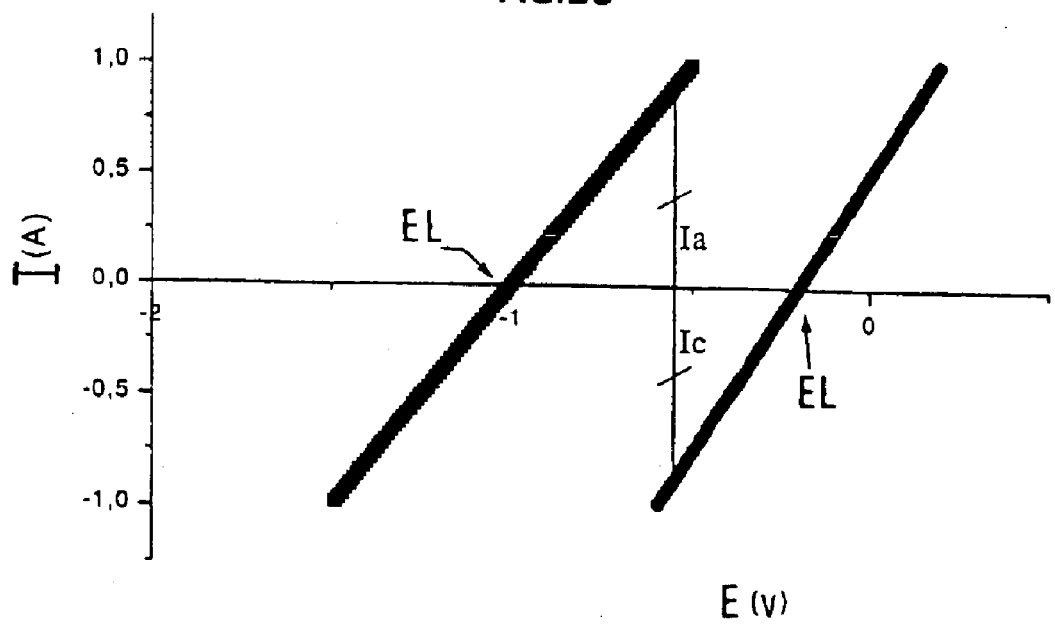
FIG. 2c shows graph I=f(E) in the coupling stage.
Figure 2A:
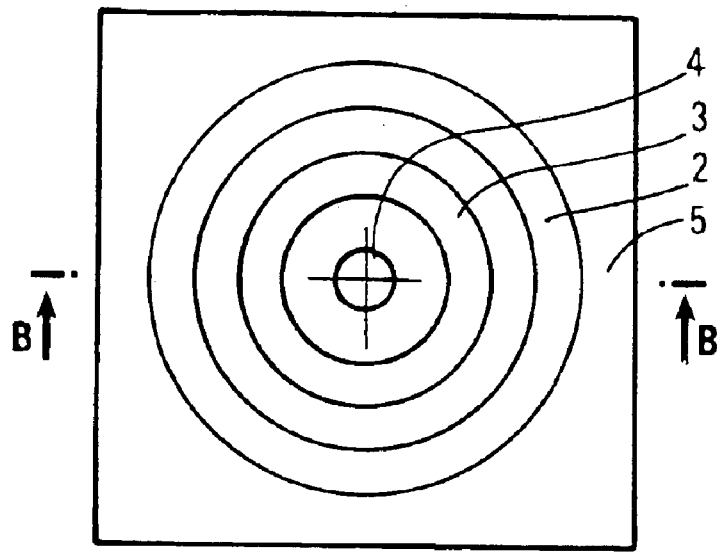
FIGS. 2a and 2b show a detector according to the invention.
Figure 2B:
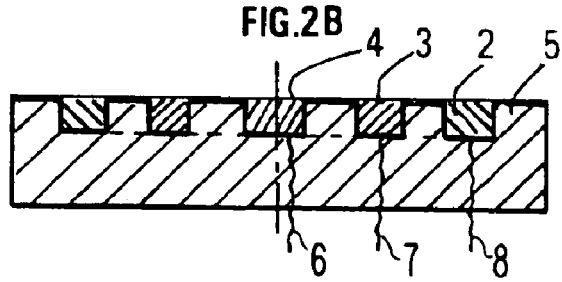

FIG. 2a is a top view of a detector and FIG. 2b a cross-sectional view of the detector in a plane of symmetry.

The detector has two rings 2 and 3 and a disk 4, all metallic and concentric. The geometrical dimensions are given in the non-limitative table hereafter. Two geometries are currently used in the laboratory.

| DETECTOR 1 | | | |
|---|---|---|---|
| | Outside diameter (mm) | Inside diameter (mm) | Surface area (mm²) |
| Large electrode (2) | 30 | 22 | 326 |
| Intermediate electrode (3) | 10 | 4 | 66.0 |
| Small electrode (4) | 2 | — | 3.14 |

| DETECTOR 2 | | | |
|---|---|---|---|
| | Outside diameter (mm) | Inside diameter (mm) | Surface area (mm²) |
| Large electrode (2) | 25 | 18 | 237 |
| Intermediate electrode (3) | 11 | 8 | 44 |
| Small electrode (4) | 1 | — | 0.785 |

The metal rings are made of carbon steel (Designation: API5L, grade 50D) and they are embedded in a cold setting epoxy resin matrix 5. The detector is then machined in order to obtain a plane surface. Electrical wires 6, 7, 8 are set prior to casting the resin. They will thereafter allow imposing or to follow the electrochemical constants relative to the metal surfaces during an in-situ or laboratory experiment.

The reason for the presence of auxiliary ring 3 is that it can be used to prevent short-circuit risks due to the iron sulfide FeS deposit, and prevents applying too high a current density to the cathodic part (small electrode 4).

The metallic material of the electrodes can be suited to the metallic material of the structure whose corrosion is to be monitored so as to optimize correlations between the information provided by the detector and the effective corrosion on the structure. It is possible to use the material of the structure for the electrodes of the detector.

Applying a preconditioning current to polarize the two electrodes leads to obtaining an electrode that becomes cathode and the other anode (by comparing the corrosion potentials).

According to the invention, three metal surfaces are used, the two rings 2 and 3, and disk 4. During a preconditioning stage, two of the three electrodes are short-circuited. The current density i (i=impressed current/electrode surface area) of the anodic and cathodic parts can thus be adjusted so that their ratio is 5 at most. In fact, it is desirable that, during this stage, the cathodic current density on the electrodes is above $0.5 \, \mu A/mm^2$. The cathodic current density on the electrodes preferably ranges between 0.5 and $5 \, \mu A/mm^2$, and more preferably between 0.5 and $2 \, \mu A/mm^2$. The surface area of disk 4 is generally small and the auxiliary electrode is usually connected to the central electrode.

The second stage of the experiment is a short-circuiting of two of the three electrodes. The circulating current is then referred to as corrosion current (I corrosion) and the process can be diagrammatically illustrated by FIG. 2c, where I corrosion=Ia=|Ic|.

The electrode with the lowest free potential reacts upon coupling like an anode since operation is the anodic part of curve I/E. On the other hand, for the electrode with the highest free potential, its behavior is cathodic since, during coupling, the cathodic part of curve I/E is swept.

Corrosion can thus be initiated and also localized, which is a definite advantage. Since the corrosion rate is directly proportional to the corrosion current and inversely proportional to the corroded surface area, the main advantage is that the value of the corrosion current and the corrosion rate can be correlated. The value of the surface area of the corroded surface therefore has to be as close as possible to the value of the surface area of the electrode in question.

For information only, the analytical expression of the corrosion rate as a function of the corrosion current and of the corroded surface area as follows:

$$V_{corrosion} = 1.1 \frac{I_{corrosion}}{Surface \ area_{corroded}}$$

where:

| | |
|---|---|
| $V_{corrosion}$ | corrosion rate in mm/year |
| $I_{corrosion}$ | corrosion current in $\mu A$ |
| Surface area$_{corroded}$ | area of the corroded surface in mm². |

Corrosion is first initiated electrochemically (FIG. 2c) and the corrosion, whether uniform or localized, develops and is sustained by the bacterial growth at the surface of the electrode.

In short, the purpose of the invention is to initiate and to localize corrosion on a metal surface. According to electrochemistry, if it is desired to develop and notably to quantify a microbiologically induced corrosion, this corrosion has to be initiated on a small surface in order to have the best possible correlation between the circulating corrosion current and the corrosion rate. This small surface therefore has to be polarized as an anode during the first stage of the experiment.

From a microbiological viewpoint, as bacterial growth occurs more readily on the cathodic part, a more sizeable biofilm forms on the small surface, which allows initiation of a microbiologically induced corrosion that is more extensive than anywhere else.

The auxiliary electrode interposed between disk 4 and ring 2 is also advantageous for monitoring the state of the detector during the coupling stage, during which sulfide deposits can eventually short-circuit the two electrodes. In fact, it is possible to check if the sulfide deposit has annihilated the detector by testing the potential of the auxiliary electrode.

The following example, given by way of illustration, allows to better understand the advantages of the present invention.

The culture media are prepared in two different vessels in order to prevent precipitation of certain salts. The media are prepared with demineralized water and the pH values of the solutions are adjusted with 4N hydrochloric acid. For the bacterial culture, two vessels are used whose compositions are as follows:

7.5-liter vessel

| | |
|---|---|
| Sodium sulfate $Na_2SO_4$ | 20 g |
| Potassium hydrogen carbonate $KHCO_3$ | 2 g |
| Hepta hydrated magnesium sulfate $MgSO_4, 7H_2O$ | 40 g |
| Sodium chloride NaCl | 300 g |
| Ammonium chloride | 10 g |

-continued

| | |
|---|---|
| Yeast extract | 2.5 g |
| Dihydrated calcium chloride CaCl$_2$,2H$_2$O | 1 g |
| Demineralized water, q.s. | 7.5 l |

The pH value of the solution is adjusted to 6.15 with the 4N hydrochloric acid.

2.5-liter vessel

| | |
|---|---|
| Potassium hydrogen phosphate KH$_2$PO$_4$ | 5 g |
| Sodium lactate, 50% solution | 36 ml |
| Hepta hydrated iron sulfate, 1 g/l solution, FeSO$_4$,7H$_2$O | 1.5 ml |
| Demineralized water, q.s. | 2.5 l |

The pH value of the solution is adjusted to 7.40 with the 4N hydrochloric acid.

The medium coming from the reactor is called bacterial medium (B.M.) because it contains bacteria, whereas the media described above are referred to as fresh media (F.M.).

Two hydrostatic pumps are used for feeding F.M. to the culture reactor: the pump intended for the 7.5-liter vessel has a flow rate of 37.5 ml/hour, the pump intended for the 2.5-liter vessel has a flow rate of 12.5 ml/hour. The reactor in which the bacterial strain is cultured being of 1 liter volume, the complete volume of the reactor is renewed every 20 hours.

Experimental conditions

Concerning the experimental conditions of the reactor in which the bacterial strain is cultured, the culture temperature is set at 37° C. and the pH value of the solution is 7.4 after adding 2N sulfuric acid. A 400-rpm rotation is maintained in the reactor to prevent the formation of a biofilm on the reactor walls and to homogenize the culture medium.

A nitrogen stream sweeps the top of the fermenter in order to eliminate the hydrogen sulfide that inhibits the bacterial development.

Figure 3:
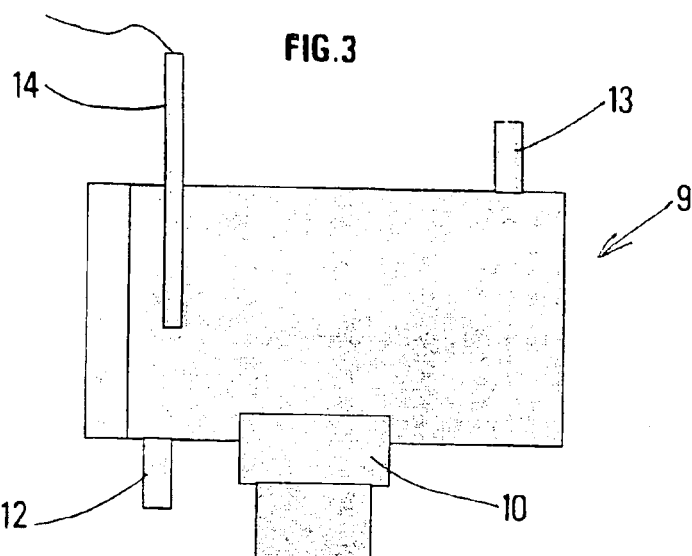
FIG. 3 illustrates the experimental means.

Electrochemistry cell (9) of FIG. 3 comprises corrosion detector (10), an inlet line (12), an outlet line (13) and a reference electrode (14). Cell (9) is installed in a thermostat-controlled drier at 37.4° C.

The corrosion detector is smoothed with a 180, then a 1200 abrasive paper, degreased with acetone and washed with alcohol.

The experiment is carried out in three stages:

Preconditioning stage

Figure 4:
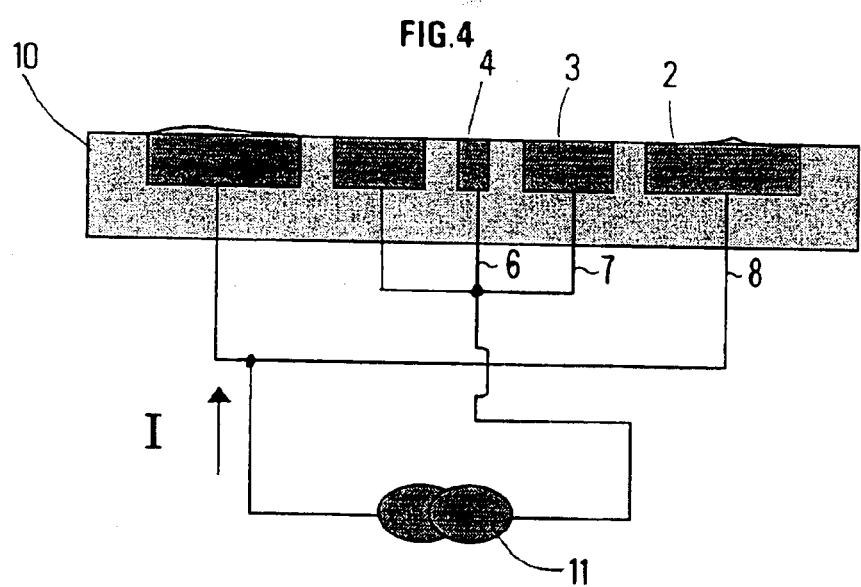
FIGS. 4 and 5 show the connections of the detector for the conditioning and coupling stages.

The plexiglas cell (FIG. 3) that contains corrosion detector (10) is supplied with bacterial medium. According to FIG. 4, central electrode (4) and intermediate electrode (3) are both connected to one of the terminals of galvanostat (11) so that small electrode (4) (and auxiliary electrode (3) associated therewith) is a cathode and large electrode (2) is an anode. The minimum length of this stage is about two days. It preferably ranges between 2 and 30 days, and more preferably between 2 and 5 days. During this stage, current-voltage curves are drawn and electrochemical constants (potentials of the various metal surfaces) are recorded.

Fresh medium supply stage

The purpose of this stage is to promote the bacterial growth at the surface of the detector. It is carried out by deconnecting the bacterial medium supply and by connecting a fresh medium supply. A 70-µA current is still applied. Meanwhile, the electrochemical constants are recorded and the bacterial growth is detected by a potential jump of the cathodically polarized electrode. This potential jump depends on the preconditioning current. For preconditioning current density values above 0.5 µA/mm$^2$, no potential jump is detected. On the other hand, for a preconditioning current density of the order of 0.21 µA/mm$^2$, the jump is observed within the 24 hours after the fresh medium supply.

Coupling stage

Figure 5:
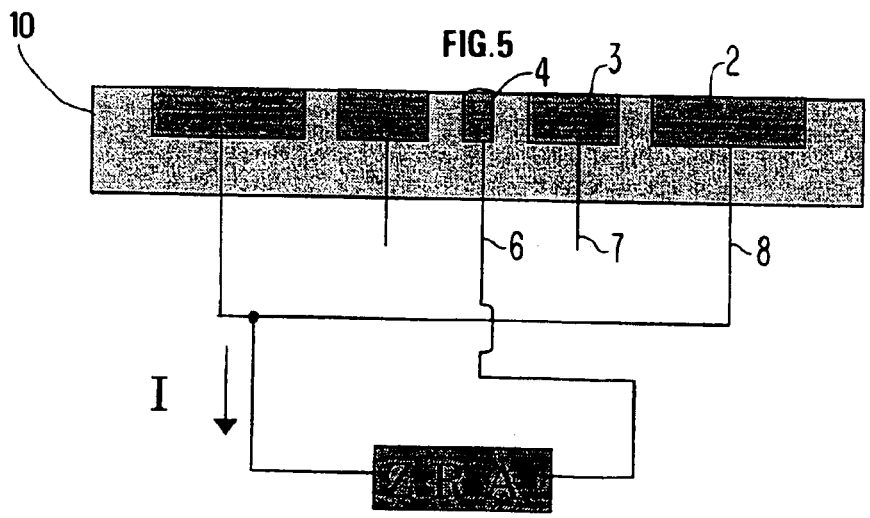

According to FIG. 5, this stage is carried out by short-circuiting small electrode (4) and large electrode (2) and intermediate electrode (3) being then disconnected. This short-circuit is obtained using a ZRA (Zero Resistance Ammeter) or a potentiostat at the input terminals of which a zero potential difference is applied. Corrosion is thus started.

The corrosion current variations and the potentials of the various electrodes in the course of time are then followed. This stage lasts for at least 4 days. The experiment can be continued as long as necessary.

It can be noted that the metal surface that was cathode in the first preconditioning stage becomes anode in the last coupling stage (and conversely). We thus have a current circulation reversal.

Comments

A whitish deposit characteristic of the formation of a biofilm can be observed at the surface of the detector. Bacteria have thus definitely deposited, but the preconditioning is such that black precipitates are observed at the surface of the anodically polarized electrode; this is in accordance with electrochemistry, as the dissolved iron is found again as ferrous ions. These ferrous ions react with the sulfide present in the medium according to the reaction as follows:

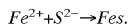

$$Fe^{2+}+S^{2-} \rightarrow Fes.$$

The resulting product (FeS) is black, which can also be noticed when observing the surface of the detector.

At the end of the first stage, the potential difference between the two polarized parts is about 675 mV. When shifting to the fresh medium supply stage, this difference decreases and reaches about 600 mV. When the stability of the value of this difference is reached, the coupling stage is carried out. The recorded corrosion current has a value of 30 µA, then it drops very quickly and reaches a value ranging between 10 and 25 µA (which represents a corrosion rate of about 6 mm/year). The change in the electrochemical behavior of the preconditioned electrodes is observed: the large anode polarized electrode becomes a cathode during coupling and the small cathode polarized electrode becomes anode during coupling, which meets the corrosion measurement criteria considered.

FIG. 6 shows the results consisting of the electrochemical parameters recorded during a complete biocorrosion experiment. In the graph of FIG. 6, abscissa T is graduated in days, ordinate ddp (potential difference) in volts, Vcor (corrosion rate) in millimeters per year.

From 0 to 5 days, graph 20 represents the preconditioning stage, from 5 to 7 days graph portion 21 represents the fresh medium supply stage, and from 7 days to the end, the coupling stage is represented by curve 22.

Thus, the detector according to the invention, used with the method described, allows detection of corrosion due to the presence of bacteria. In the case where the corrosion is not sustained by the bacterial metabolism, for example during a laboratory experiment, the corrosion rate signal decays very quickly (in less than two days).

The detector and the implementation stages carried out to observe the microbiologically induced corrosion answer the questions that must be considered in the field of deterioration of industrial metal structures by microorganisms.

When bacteria can accelerate a corrosion on a metal surface, it is possible to localize this corrosion on a specific metal surface and to record the current linked with this corrosion.

This system can detect and prevent any risk of corrosion damage to metal structures of industrial sites.

| Test number | 000 | Detector used | 1 |
|---|---|---|---|
| Preconditioning | | | |
| Impressed current | 69 μA | | |
| Anode: small and auxiliary | Cathode: large | | |
| Fresh medium supply | Yes | | |
| Potential jump observed | Yes | | |
| Coupling | | | |
| Short-circuited electrodes | Small and large | | |
| | The small electrode is cathode | | |
| Corrosion current | 3 μA | | |

This first test allows to check that the direction of the corrosion current is opposite to that of the preconditioning current.

| Test number | 100 | Detector used | 1 |
|---|---|---|---|
| Preconditioning | | | |
| Impressed current | 70 μA | | |
| Anode: large | Cathode: small and auxiliary | | |
| Fresh medium supply | Yes | | |
| Potential jump observed | Yes, but weak | | |
| Coupling | | | |
| Short-circuited electrodes | Small and large | | |
| | The small electrode is anode | | |
| Corrosion current | 20 μA | | |

This test corresponds to the invention where the small electrode is anode during coupling.

| Test number | 200 | Detector used | 1 |
|---|---|---|---|
| Preconditioning | | | |
| Impressed current | 70 μA | | |
| Anode: auxiliary | Cathode: large | | |
| Fresh medium supply | Yes | | |
| Potential jump observed | Yes | | |
| Coupling | | | |
| Short-circuited electrodes | Small and large | | |
| Corrosion current | Too weak to give a direction to the corrosion current | | |

This test allows to check that the small electrode has to be conditioned.

| Test number | 400 | Detector used | 1 |
|---|---|---|---|
| The auxiliary and the large electrode are coated with a membrane porous to ionic species | | | |
| Preconditioning | | | |
| Impressed current | 3 μA | | |
| Anode additional electrode | Cathode: small | | |
| Fresh medium supply | Yes | | |
| Potential jump observed | No | | |

| Test number | 400 | Detector used | 1 |
|---|---|---|---|
| Coupling | | | |
| Short-circuited electrodes | Coated auxiliary and large | | |
| | The large electrode is anode | | |
| Corrosion current | Very weak | | |

This test allows to check that all the electrodes have to he conditioned.

| Test number | 600 | Detector used | 1 |
|---|---|---|---|
| Preconditioning | | | |
| Impressed current | 14 μA | | |
| Anode: large | Cathode: small and auxiliary | | |
| Fresh medium supply | Yes | | |
| Potential jump observed | Yes | | |
| Coupling | | | |
| Short-circuited electrodes | Small and large | | |
| | The small electrode is anode, then cathode | | |
| Corrosion current | In absolute value, 2 μA at the start and 4 μA at the end | | |

This test allows to check that too weak a preconditioning current can be insufficient to create a coupling.

| Test number | 700 | Detector used | 1 |
|---|---|---|---|
| Preconditioning | | | |
| Impressed current | 48 μA | | |
| Anode: auxiliary | Cathode: small and large | | |
| Fresh medium supply | Yes | | |
| Potential jump observed | Yes | | |
| Coupling | | | |
| Short-circuited electrodes | Small and auxiliary | | |
| | The small electrode is anode, then the short-circuit is generated | | |
| Corrosion current | 4 μA | | |

This test allows checking that the geometry of the rings has no effect on the corrosion but that, if the two electrodes are too close to one another, they can be quickly short-circuited.

Example of application to an industrial facility

Figure 7:
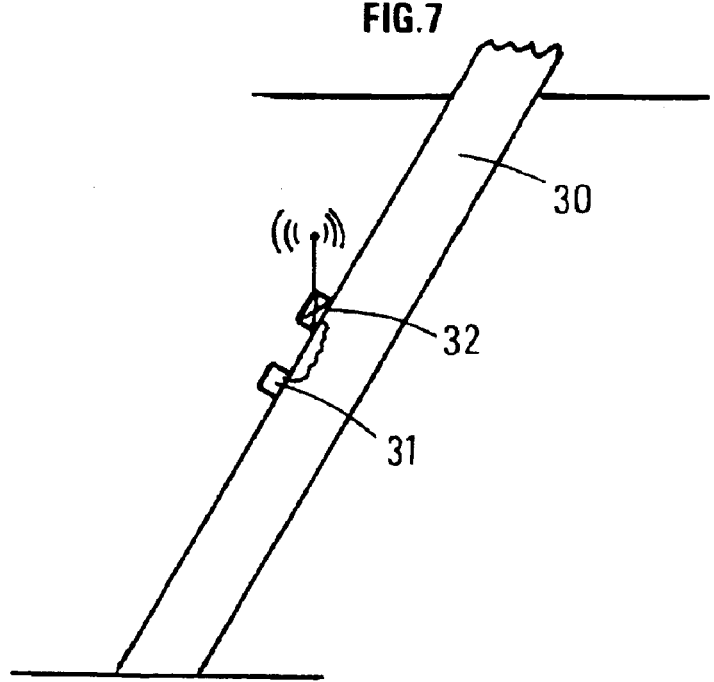

The detector according to the invention is placed on a metal structure whose corrosion is to be monitored. FIG. 7 shows a structure 30, for example a tubular element that constitutes the leg of an offshore platform. A detector 31 according to the invention is placed on the tube (metal parts exposed to the outside) and it is connected to self-contained electronic means 32 intended to apply the conditioning stages and to communicate the measurements.

Another application of the present detector is placement in a pipeline so that the metal parts of the detector are exposed to the inside of the pipe.

What is claimed is:

1. A method for detection of microbiologically induced corrosion of a metal structure, comprising:
   installing a detector comprising at least a central electrode and an annular electrode concentric to the first electrode relative to the structure in contact with a corrosive medium;

applying a conditioning current for a time t between the central electrode and the annular electrode to initiate the microbiological corrosion, the current being such that the central electrode is a cathode and the annular electrode is an anode;

short circuiting, after time t, the central and annular electrodes together and measuring current and/or a potential difference between the central and annular electrodes; and calculating a corrosion rate from the measurement.

2. A method as claimed in claim 1, wherein:

the detector comprises an annular auxiliary electrode interposed between the central and annular electrodes, the annular auxiliary electrode is connected to the central electrode during applying the conditioning current and then insulated from other electrodes during the short circuiting of the central and annular electrodes.

3. A method as claimed in claim 2, wherein:

a potential difference between the central electrode and/or of the annular electrode relative to the auxiliary electrode is measured during the short circuiting of the central and annular electrode.

4. A detector for detection of microbiologically induced corrosion of a metal structure, comprising:

a central electrode;

an annular electrode concentric to the central electrode;

means for applying a conditioning current between the electrodes to initiate the microbiological corrosion, the current being such that the central electrode is a cathode and the annular electrode is an anode; and means for short circuiting the electrodes together after applying the conditioning current and for measuring current and/or a potential difference between the electrodes.

5. A detector as claimed in claim 4, comprising:

an annular auxiliary electrode between the central and annular electrode.

6. A detector as claimed in claim 5, wherein:

the means for short circuiting and applying a current and the means for measuring are self-contained and apply the conditioning current and communicate measurements of the current and/or potential difference.

7. A detector as claimed in claim 6, wherein:

the electrodes comprise a material comprising the metal structure.

8. A detector as claimed in claim 5, wherein:

the electrodes comprise a material comprising the metal structure.

9. A detector as claimed in claim 4, wherein:

the means for short circuiting and applying a current and the means for measuring are self-contained and apply the conditioning current and communicate measurements of the current and/or potential difference.

10. A detector as claimed in claim 9, wherein:

the electrodes comprise a material comprising the metal structure.

11. A detector as claimed in claim 4, wherein:

the electrodes comprise a material comprising the metal structure.

* * * * *